United States Patent
Weil et al.

(10) Patent No.: US 6,821,254 B2
(45) Date of Patent: Nov. 23, 2004

(54) CARDIAC/RESPIRATORY ARREST DETECTOR

(75) Inventors: Max Harry Weil, Northbrook, IL (US); Joe Bisera, Camarillo, CA (US); Wanchun Tang, Palm Desert, CA (US)

(73) Assignee: Institute of Critical Care Medicine, Palm Springs, CA (US)

( * ) Notice: Subject to any disclaimer, the term of this patent is extended or adjusted under 35 U.S.C. 154(b) by 353 days.

(21) Appl. No.: 09/894,572

(22) Filed: Jun. 27, 2001

(65) Prior Publication Data

US 2002/0032383 A1 Mar. 14, 2002

Related U.S. Application Data

(60) Provisional application No. 60/220,120, filed on Jul. 21, 2000.

(51) Int. Cl.[7] .................................................. A61B 5/08
(52) U.S. Cl. ........................ 600/484; 600/547; 600/529; 600/508
(58) Field of Search ................................. 600/484, 547, 600/529, 533, 508, 509, 513

(56) References Cited

U.S. PATENT DOCUMENTS

| 3,524,058 | A | | 8/1970 | Robertson et al. | |
|---|---|---|---|---|---|
| 3,727,604 | A | | 4/1973 | Sidwell et al. | |
| 3,750,649 | A | | 8/1973 | Severinghaus | |
| 3,901,214 | A | | 8/1975 | Taaffe | |
| 4,517,982 | A | * | 5/1985 | Shiga et al. | 600/484 |
| 5,170,794 | A | | 12/1992 | Reiche | |
| 5,335,666 | A | | 8/1994 | Bowman et al. | |
| 5,348,008 | A | * | 9/1994 | Bornn et al. | 600/484 |
| 5,353,793 | A | * | 10/1994 | Bornn | 600/508 |
| 5,505,209 | A | | 4/1996 | Reining | |
| 5,564,429 | A | * | 10/1996 | Bornn et al. | 600/508 |
| 5,632,280 | A | * | 5/1997 | Leyde et al. | 600/508 |
| 6,011,992 | A | | 1/2000 | Hubbard et al. | |
| 6,440,082 | B1 | * | 8/2002 | Joo et al. | 600/509 |

FOREIGN PATENT DOCUMENTS

WO    WO 99/30773    6/1999

* cited by examiner

Primary Examiner—Fadi H. Dahbour
(74) Attorney, Agent, or Firm—Leon D. Rosen

(57) ABSTRACT

The condition of a patient who has signs of cardiopulmonary arrest, is evaluated by applying a pair of electrodes (12, 14) to the chest of the patient and passing a low level of alternating current through the patient to detect changes in transthoracic impedance which represent cardiopulmonary activity of the patient. An analyzing circuit determines the average frequency of those signals (40) representing heartbeat rate impedance and determines the average frequency of signals (42) representing breathing of the patient. When the heart rate is below about 20 beats per minutes, the respiratory rate is below about 4 breaths per minute, and cardiac and respiratory impedances are below 0.01 ohms, this indicates cardiac arrest of the patient and signifies that CPR (cardiopulmonary resuscitation) should start.

13 Claims, 7 Drawing Sheets

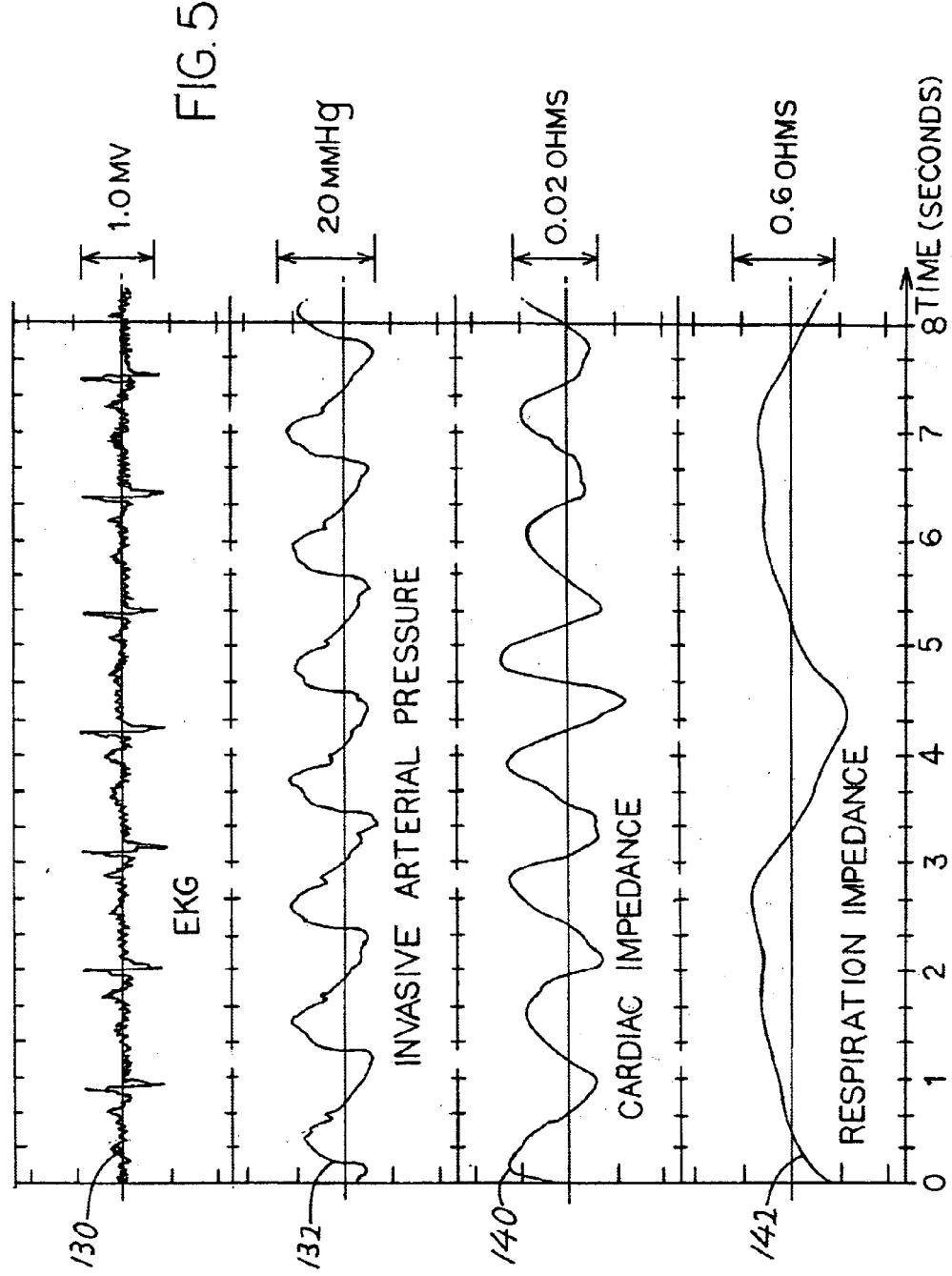

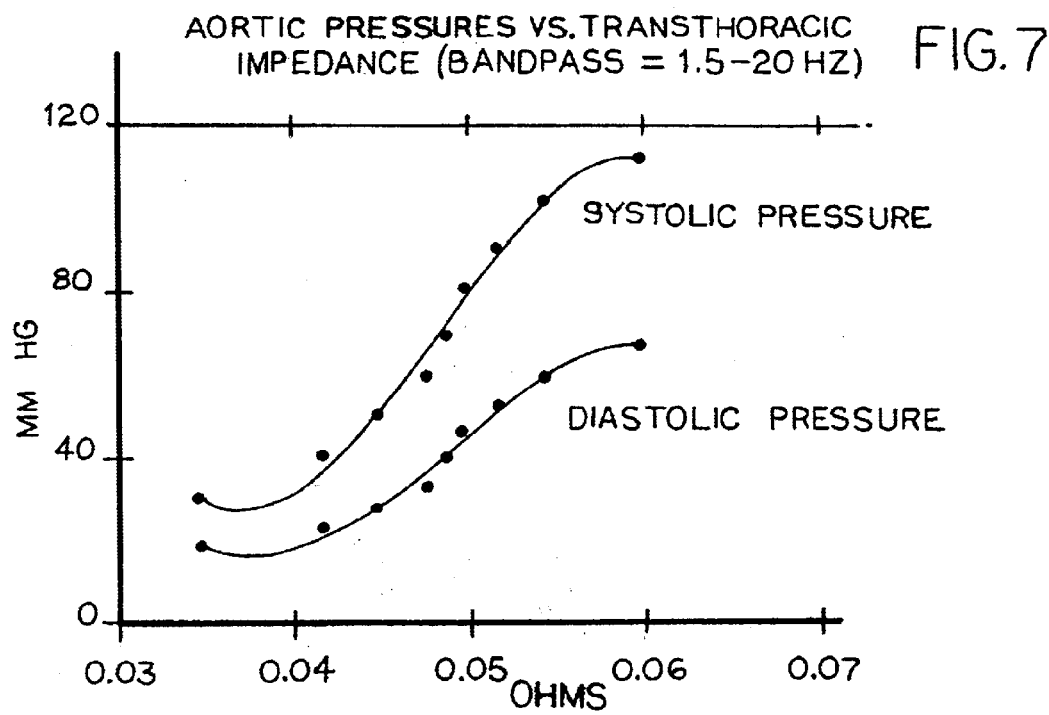
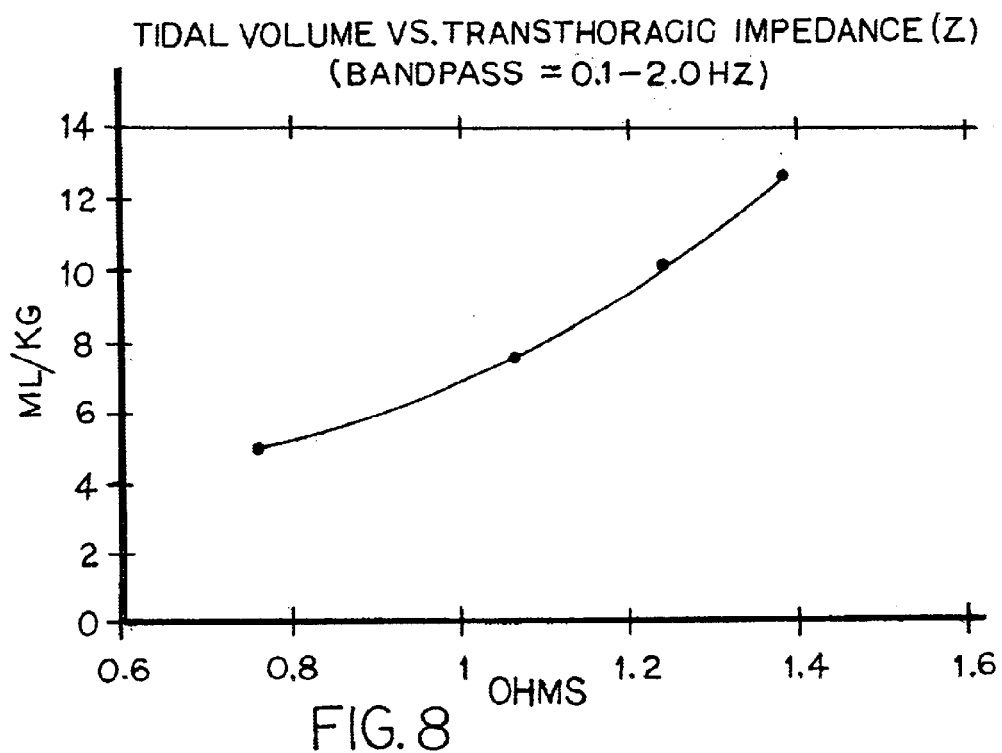

CARDIAC/RESPIRATORY ARREST DETECTOR

CROSS-REFERENCE

Applicant claims priority from provisional application 60/220,120 filed Jul. 21, 2000.

BACKGROUND OF THE INVENTION

It is often necessary for a person who is not a medical professional, to evaluate the condition of a weak patient who has signs of cardiopulmonary arrest, especially when the patient is partly or completely unconscious. One of the first steps of a rescuer is to determine if there is sufficient breathing and adequate blood circulation. Unfortunately, evaluation of these two parameters is difficult. For identification of blood circulation by detecting a pulse, a common method is to place a hand on a region of the body (e.g. carotid artery) and feel for small fluctuations. For evaluation of breathing, a common method is to place the rescuer's face near the mouth to feel or hear the flow of air or movement of the chest. Although detection of pulse and breathing is not difficult in normal patients, such identification is difficult in weak patients, such as a patient in shock, where there is low flow of blood and of air. The inability to detect pulse and respiration at this time increases the probability of an incorrect diagnosis between cardiac arrest, breathing arrhythmia (irregular heartbeat), or asphyxia. The consensus of investigators of cardiopulmonary resuscitation is that current "pulse check" has less than a fifty percent accuracy in identifying cardiac arrest.

An apparatus and method that facilitated a determination of the cardiac and pulmonary functions of a patient, by persons who are not medical professions, and by noninvasive means, would be of value.

Two other parameters useful in medical diagnoses by medical professionals, is the blood pressure (both systolic and diastolic) and the volume of air in each breath. For normal patents (those who are not weak) blood pressure can be taken by a cuff that fits around the arm, and breathing volume can be measured by having a patient breath out into a container. This is not possible for a weak patient. An apparatus and method that enabled such measurements by noninvasive means, would be of value.

SUMMARY OF THE INVENTION

In accordance with one embodiment of the present invention, a method and apparatus are provided for evaluating the condition of a patient who is weak, such as one who has symptoms of cardiopulmonary arrest. Alternating current of a frequency between about 1 kHz and 90 kHz is applied between two electrodes lying at opposite sides of the chest of the patient. Variations in voltage are measured to detect variations in impedance of the patient's chest area. Such variations are primarily due to activity of the heart and respiration system. An analyzing circuit determines the average amplitude and frequency of those signals representing heartbeats, and preferably also determines the amplitude and frequency of signals representing respiration.

If the respiratory rate is less than about 4 breaths per minute and the heart rate is less than about 20 beats per minute, then this indicates cardiac arrest. A care giver who is ready to perform CPR (cardiopulmonary resuscitation) can use the information about the patient's status, to emphasize chest compressions to simulate cardiac activity, or concentrate on applying quantities of air to the patient's lungs to emphasize breathing. The fact that heartbeats and/or breathing can be detected, provides encouragement to the care giver.

A separation of the signal components representing cardiac activity from those representing respiration, and from those representing extraneous signals, is accomplished by filtering the demodulated alternating current passing through the patient's chest. Those frequencies above about 0.3 Hz (18 per minute) represent cardiac activity. The portion of the demodulated signal representing respiration can be separated from that representing cardiac activity, by filtering out frequencies below about 0.25 Hz (15 breaths per minute) since a weak patient such as one having signs of cardiopulmonary arrest breathes at less than 15 breaths per minute.

The apparatus can indicate no cardiac arrest when the respiratory rate is above about 4 bpm (breaths per minute) and the heart rate is above about 20 bpm (beats per minute). A respiratory rate above about 4 bpm and heart rate less than about 20 bpm indicates no cardiac arrest but extreme breathing arrhythmia. A respiratory rate less than about 4 bpm and heart rate above about 20 bpm indicates no cardiac arrest, but possible asphyxia. A respiratory rate less than about 4 bpm and heart rate less than about 20 bpm indicates cardiac arrest.

The detected signals representing cardiac activity can be used to determine the blood pressure (systolic and diastolic) of the patent. The detected signals representing respiration can be used to determine the volume of each breath of the patient.

The novel features of the invention are set forth with particularity in the appended claims. The invention will be best understood from the following description when read in conjunction with the accompanying drawings.

BRIEF DESCRIPTION OF THE DRAWINGS

FIG. 5 is a group of four graphs showing direct EKG and direct arterial pressure measurements of a patient, and showing cardiac and respiratory impedance signals produced by the apparatus of the present invention simultaneously with the direct measurements, in a test conducted by applicants.

FIG. 7 is a chart showing variation in blood pressure, both systolic and diastolic, with cardiac impedance.

FIG. 8 is a chart showing variation in the volume of each breath per kilogram body weight, as a function of respiratory impedance.

DESCRIPTION OF THE PREFERRED EMBODIMENTS

Figure 1:
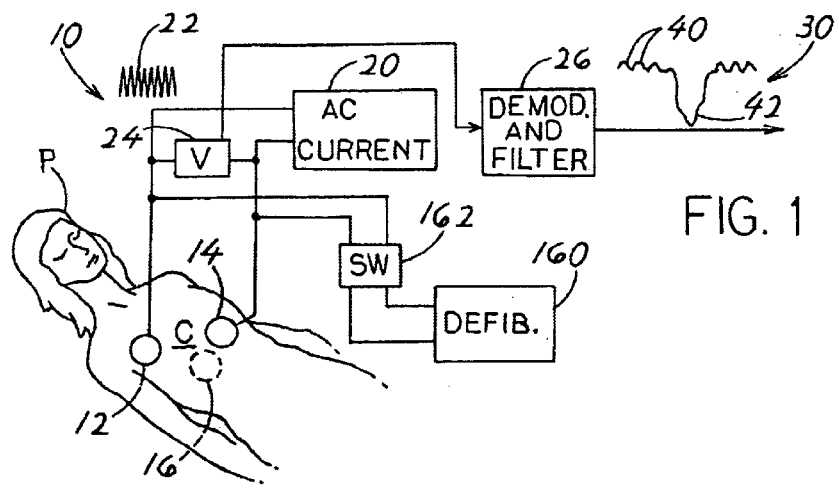
FIG. 1 is a simplified block diagram of apparatus of the present invention for evaluating the condition of a patient who has symptoms suggesting cardiopulmonary arrest.

FIG. 1 illustrates an apparatus 10 which can be applied to the chest area C of a patient P who has symptoms of cardiopulmonary arrest, to enable a determination of the patient's condition where medical professionals are not available. A pair of electrodes 12, 14 are placed at opposite sides of the patient's chest, although an additional electrode or the electrode 2 can be placed in the position 16. An AC current supply 20 supplies current, indicated at 22, that varies in amplitude, and that may or may not vary in polarity. Preferably, the RMS (root mean square) current of the source is constant. A current is applied of about 1 milliampere, so the current does not affect functioning of the patient. The level of voltage varies, and is picked up by a voltage sensor 24 which delivers this output to a demodulator and filter circuit 26. It is generally not necessary to use a sharp cutoff filter, so the amplitude of signals passing through the filter does not change rapidly with frequency. The output of the circuit 26 is a signal of the type indicated at 30, which shows variation of voltage amplitude with time, and therefore of resistance with time when a constant amplitude AC current is applied. The AC current delivered by source 20 preferably has a frequency above about 1 kHz. This is a frequency far above those of signals of interest that indicate heart and lung functioning, and is also above power line frequency (60 Hz in the U.S.). The upper frequency of the AC current is preferably below 90 kHz because at a frequency of about 100 kHz and above, there is a significant reactance component to the impedance, which applicant's circuitry does not have to account for.

The sinusoidal characteristic of the AC signal 22 is useful to facilitate the demodulation and filtering of the signal. A sinusoidal signal has few if any harmonics, while pulses with short rise and fall times produce higher frequencies, with reactances that will affect the measured impedance.

Figure 2:
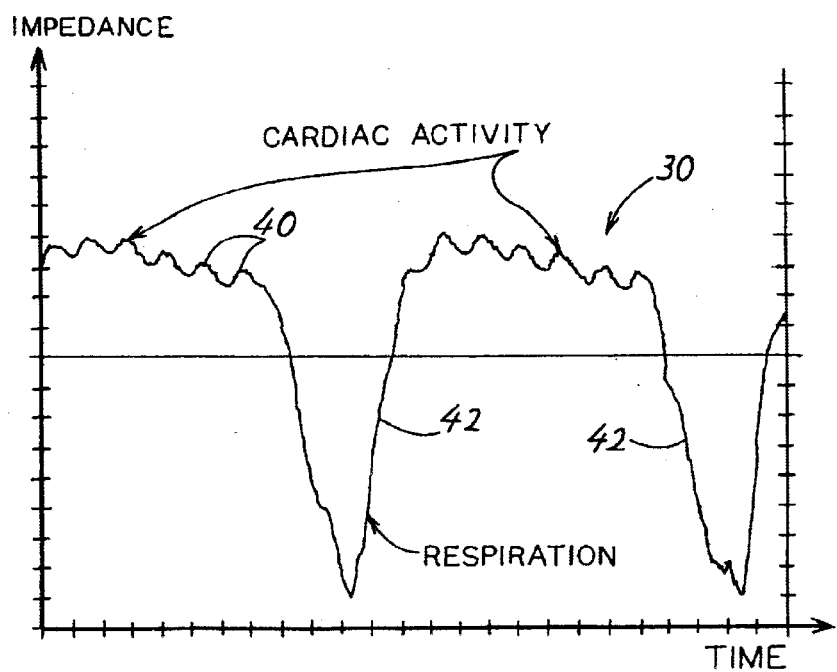
FIG. 2 is a more detailed graph showing the output signal shown in FIG. 1.

In the signal 30 shown in FIG. 2, small but rapid changes 40 indicate cardiac activity. Larger and lower frequency changes as indicated at 42, represent respiration. It can be seen that the frequency of the cardiac signals 40 is much higher than the frequency of the respiration signals 42. The cardiac signals 40 have a frequency of about 20 to 40 beats per minute for a patient showing signs of cardiopulmonary arrest. Beats at a frequency of less than about 18 bpm (frequency of 0.3 Hz) generally indicate cardiac arrest or extreme breathing arrhythmia. The respiration signals 42 are generally of a frequency of up to about 15 breaths per minute for a patient showing signs of cardiopulmonary arrest. A patient breathing more rapidly than about 15 bpm generally indicates to a care giver that he is breathing, by movements of the chest or detection of air coming from the mouth or nasal passages.

Figure 3:
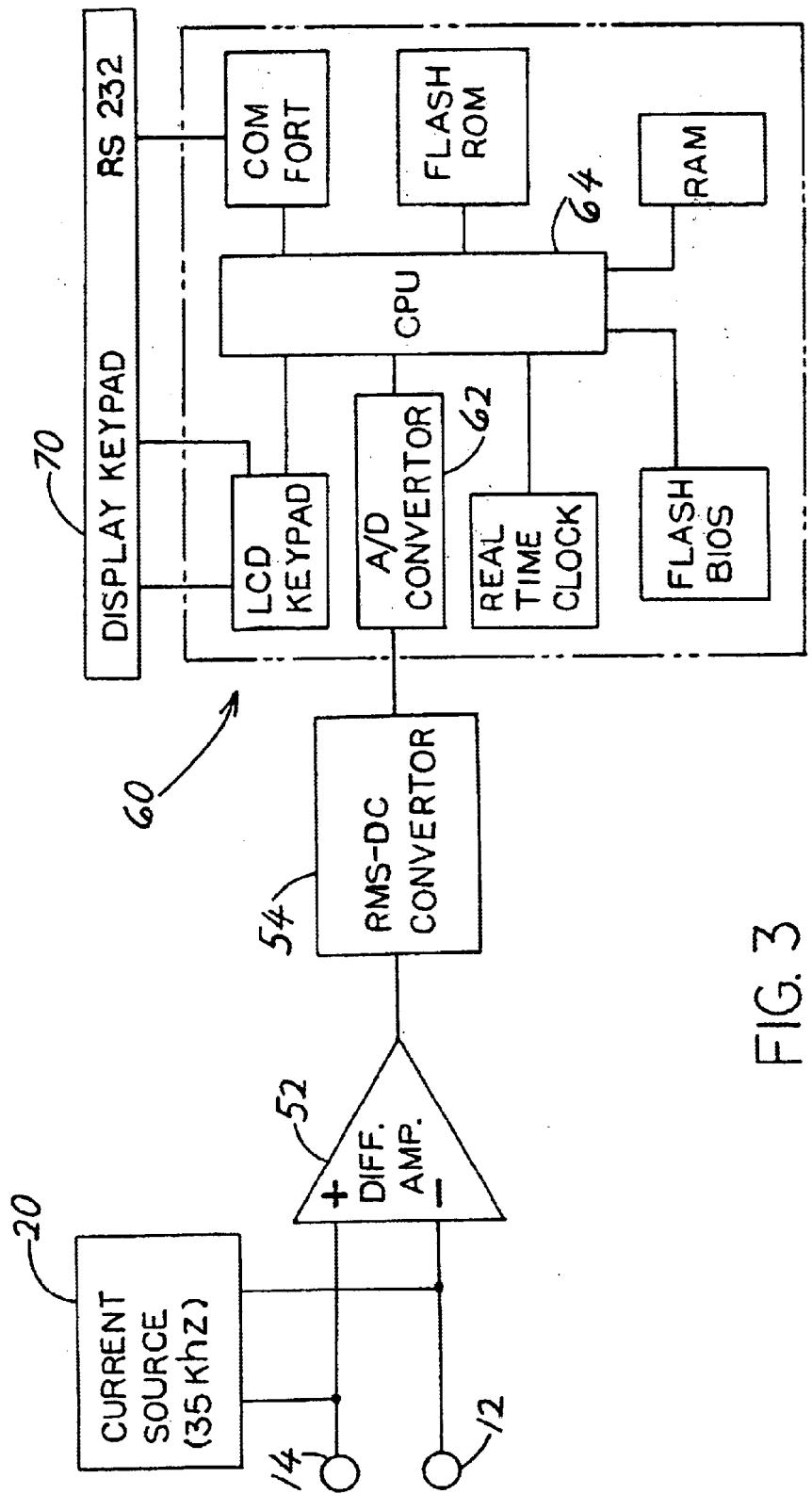
FIG. 3 is a more detailed block diagram of the circuit of FIG. 1.

FIG. 3 shows some details of a circuit 60 that applicants have designed to sense the cardiac and pulmonary condition of a patient who is showing symptoms of cardiac arrest and/or pulmonary arrest. The electrical source 20 that applicant has used, generates a frequency of 35 kHz, which is applied to the electrodes 12, 14. The electrodes are connected to a differential amplifier 52 whose output is delivered to an RMS-DC convertor 54 which demodulates and rectifies the amplifier output to deliver a low frequency signal (such as below 5 Hz) to a digital analyzing circuit 60. The signal is delivered through an A/D convertor 62 to a CPU 64. A display and keyboard combination 70 enables control and display of the results of the analysis by the circuit.

Figure 4:
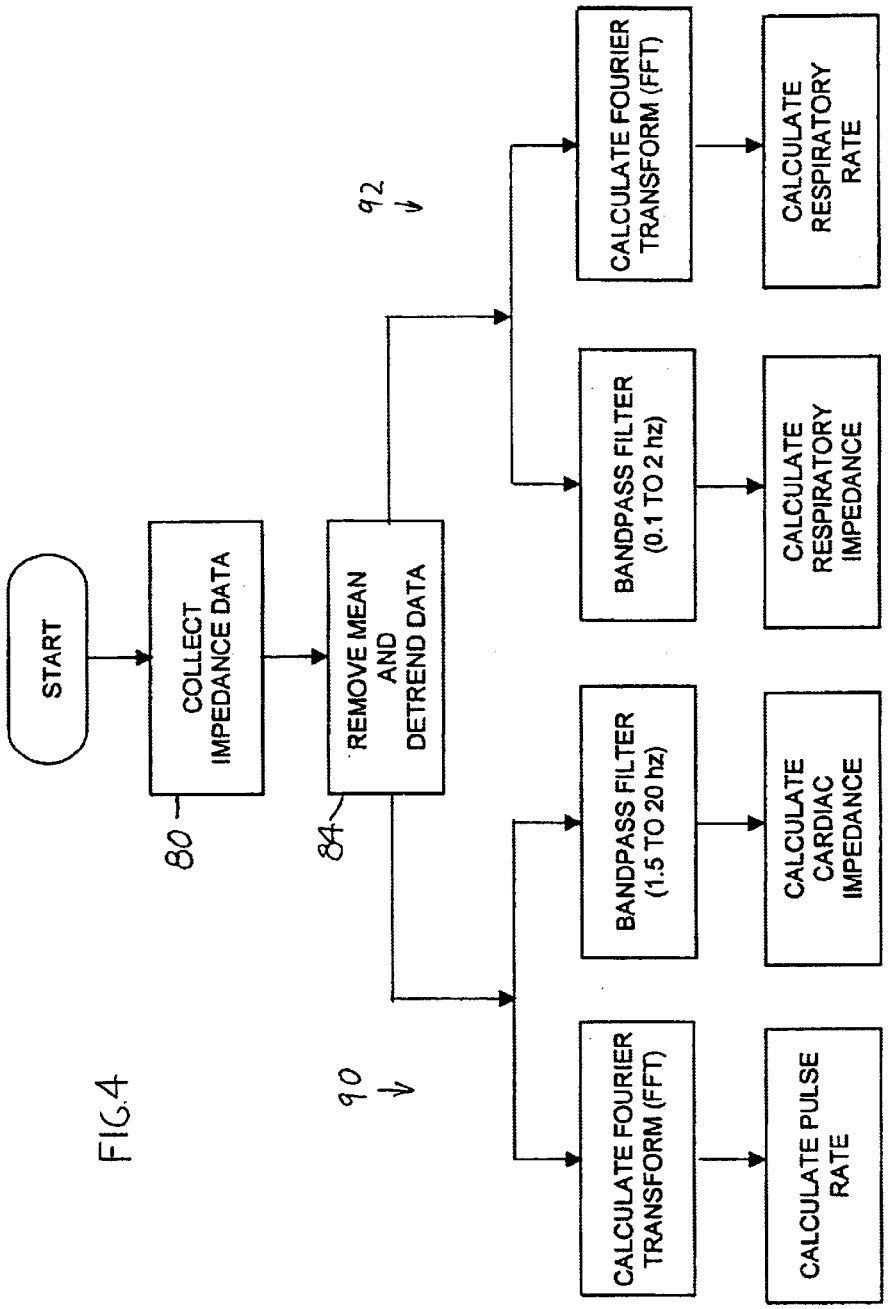
FIGS. 4 and 4A are flow charts showing analysis of impedance sensed by the circuit of FIG. 1.
Figure 4A:
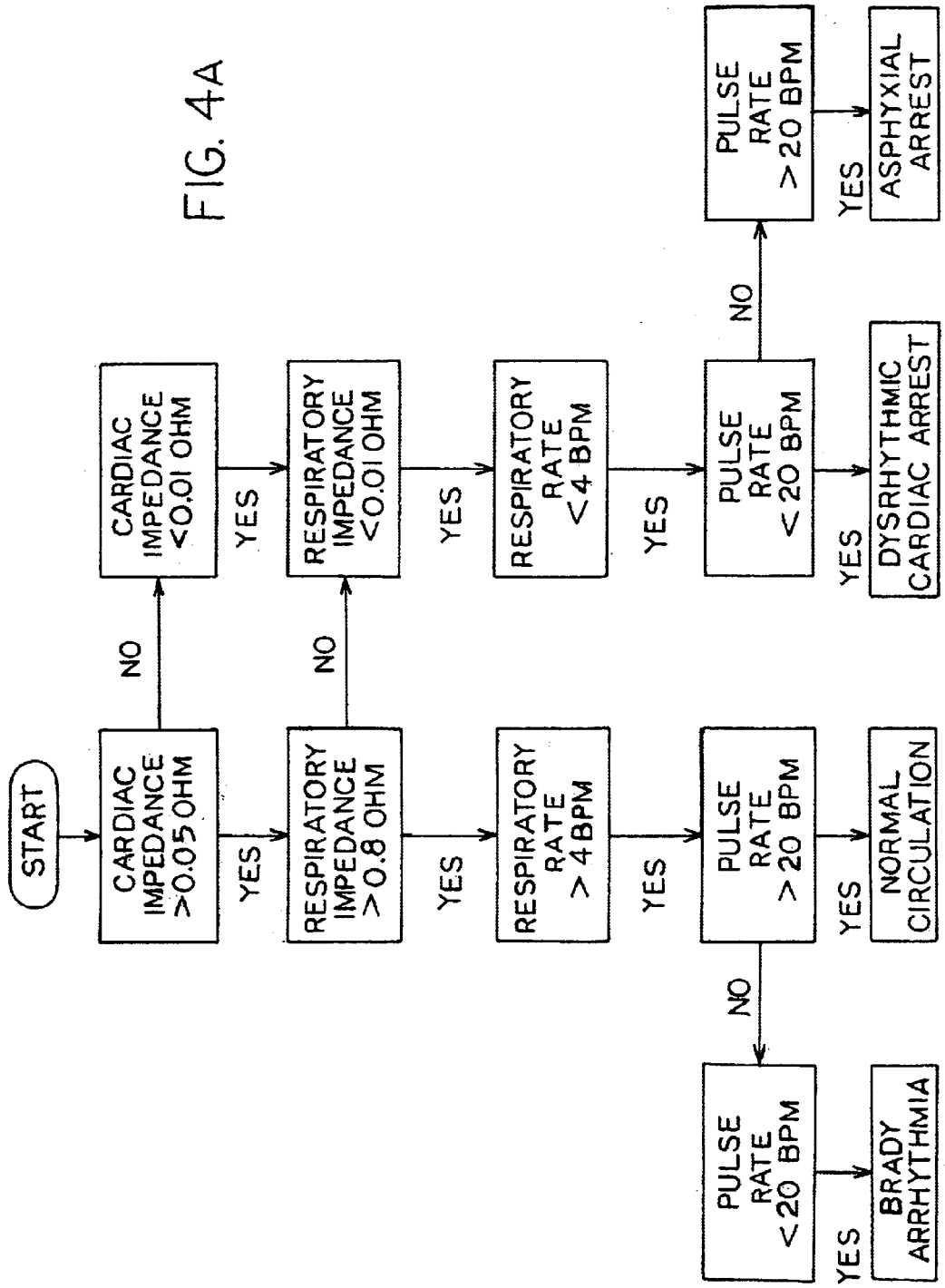

FIGS. 4 and 4A are flow charts showing the procedure for separating the respiratory signal from the cardiac activity. Respiratory and heart rate, including their respective amplitudes, are calculated and interpreted according to the following decision table. As shown in FIG. 4, the procedure begins with the collection of data at 80. At 84 mean and detrend data are removed, which is the removal of low frequencies (e.g. below about 0.1 Hz) variations. Then there is decomposition or separation, of the pulse and respiratory signals. Fourier transforms at predetermined bandpass frequencies are utilized to discriminate between respiratory breaths and heartbeat. The dominant frequency in the pass band of 0.1 to 2 Hz determines the respiratory rate and a pass band of 2 to 20 Hz is used for heartbeat. Bandpass filters are utilized to separate respiratory and cardiac impedances. Peak-to-peak amplitudes of impedances are calculate. The resultant pulse and respiratory frequencies and impedances are evaluated and used with a decision table (Table 1 given below) to determine the physiologic status of the patient. Table 1 is integrated into the flowchart (FIG. 4A) as a series of yes/no decision blocks to arrive at the correct physiological state.

TABLE 1

| STATUS | Cardiac Impedance (ohms) | Respiratory Impedance (ohms) | Respiratory Rate (bmp) | PULSE Rate (bpm) |
|---|---|---|---|---|
| Unconscious with normal circulation | >0.05 | >0.8 | >4 | >20 |
| Dysrhythmic cardiac arrest | <0.01 | <0.01 | <4 | <20 |
| Asphyxial arrest | >0.05 | <0.01 | <4 | >20 |
| Brady arrhythmia | >0.05 | >0.8 | >4 | <20 |

If the measured quantities fall outside the indicated ranges, then an indication is given that the patient's condition cannot be determined by the apparatus. For example, if the cardiac impedance is 0.01 to 0.05 ohm, or respiratory impedance is 0.01 to 0.08 ohm, then a clear determination cannot be made by the apparatus.

FIG. 1 shows that a defibrillator 160 can be connected through a switch circuit 162 to the same electrodes 12, 14 used to determine the heartbeat rate. If a heartbeat is not detectable and there is no breathing, the care giver may operate the switch circuit to begin the application of defibrillation pulses. Connections at the voltmeter and beyond are open by the switch circuit prior to defibrillation, and may be closed after a defibrillation pulse to try to detect a heartbeat.

FIG. 5 has four graphs showing electrical changes that were detected in the chest area of a patient during a test conducted by applicants, with each graph showing amplitude versus time. A first graph 130 is an EKG (electrocardiogram) which shows currents generated by the body during beating of the heart of a healthy patient. The maximum generated voltage is about 1 millivolt. Graph 132 shows changes in arterial pressure as measured by an instrument lying in the artery of the patient. The maximum change is about 20 millimeters of mercury. Graph 140 shows changes in the impedance across the chest area due to beating of the heart of a healthy patient. The change in impedance (which is substantially only resistive) is about the 0.02 ohms. For the indicated impedance and for a current of about 1 milliampere, the voltage change across the heart due to cardiac activity is about 20 millivolts.

Graph 142 shows changes in impedance due to respiration in a heathy patient who is inactive. The breaths are at a rate of about 1 every 4 to 5 seconds, or about 14 per minute. The change in impedance (all resistance) is about 0.6 ohms, which is about 30 times the change in resistance due to cardiac activity. This indicates that pulmonary activity can be differentiated from cardiac activity by the much greater change in impedance caused by pulmonary activity, in addition to the lower frequency for pulmonary activity.

Figure 6:
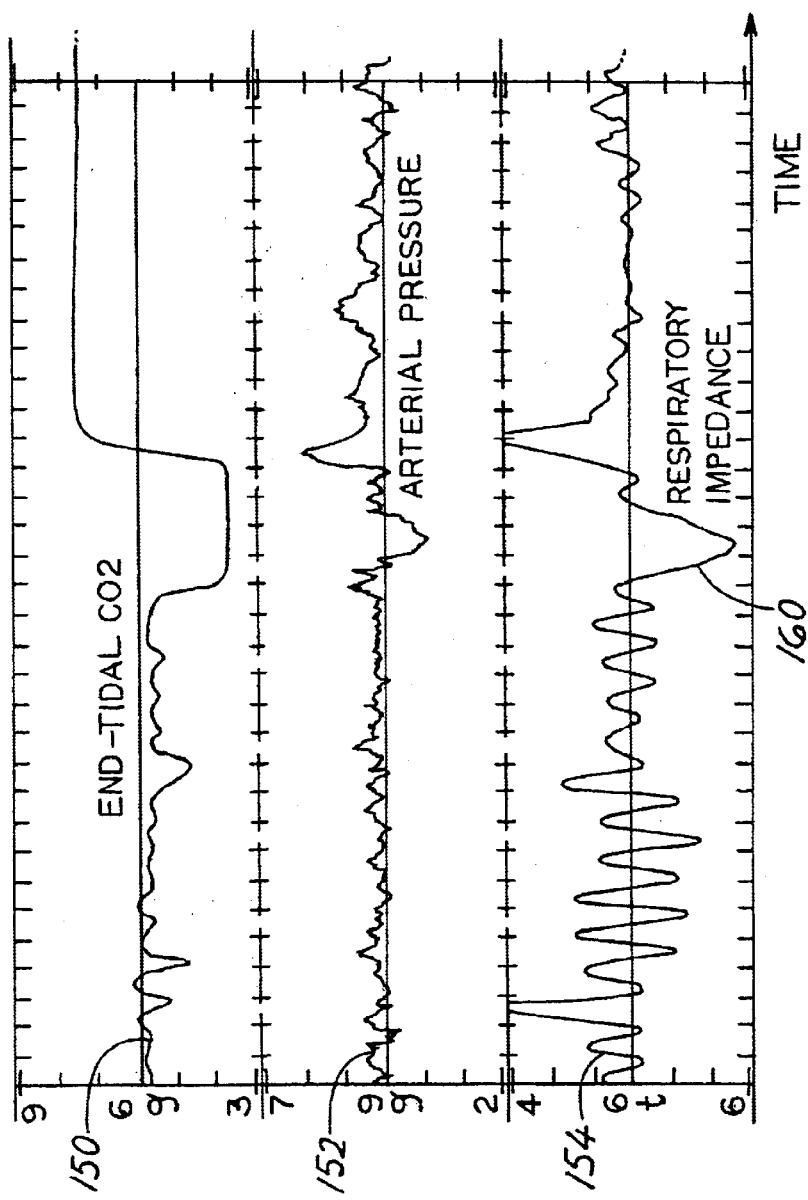
FIG. 6 is a group of three graphs showing end-tidal $CO_2$ measurements of a patient and showing cardiac and respiratory signals produced simultaneously by the apparatus of the present invention, in a test conducted by applicants.

FIG. 6 has three graphs that illustrate the use of software with a computer to detect impedance changes due to gasping of a patient. Graph 150 shows monitoring of end-tidal CO2, graph 152 shows directly measured actual arterial pressure, while graph 154 shows changes in impedance due to respiratory activity (higher frequencies due to heartbeats are filtered out). In the impedance graph 154, gasping of the patient at 160 is indicated by an unusually large drop in impedance followed by an unusually large increase in impedance, all occurring during a period more than twice the time of a breath.

Thus, the invention provides an apparatus and method for evaluating the condition of a patient who has signs of cardiac and/or respiratory failure. The apparatus includes a circuit for measuring impedance across the chest area of the patient by applying current and detecting impedance changes encountered by the current that represent cardiopulmonary activity of the patient. An analyzing circuit, which can be implemented by a computer program, determines the average frequency of heartbeats and the average frequency of respiration. It the heartbeat rate is below about 20 (15 to 25) beats per minute and the respiratory rate is below 4 (2 to 6) breaths per minute, than this indicates cardiac arrest. A heartbeat rate above about 20 per minute, with insufficient respiratory rate, or respiration above about 4 per minute with heartbeats under 20 bpm, indicates other conditions of the patient.

The circuit can determine cardiac impedance, which indicates aortic pressure by the relationship shown in FIG. 7 or equivalent formula, to indicate aortic pressure in a weak patient without an invasive catheter. The circuit can determine respiratory impedance, which indicates tital (breathing) volume by the relationship shown in FIG. 8 or an equivalent formula.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. Apparatus for evaluating the condition of a patient who has symptoms of cardiopulmonary arrest comprising:

a pair of electrodes for application to the chest of the patient:

an electricity source for applying current between said electrodes to pass through the chest of the patient;

a circuit which is coupled to said electrodes and which has an output that carries signals representing changes in impedance encountered by said current that represent cardiopulmonary activity of the patient;

an analyzing circuit with an input that receives said signal representing the cardiopulmonary activity of the patient, and which determines the average frequency of those signals representing heartbeat rate and those signals representing breathing rate; wherein said analyzing circuit indicates cardiac arrest when the average frequency of those signals representing heartbeat rate is below a predetermined rate which is about 20 beats per minutes and the average frequency of those signals representing respiratory rate is below a predetermined rate which is about 4 breaths per minute.

2. Apparatus for evaluating the condition of a patient who has symptoms of cardiopulmonary arrest comprising:

a pair of electrodes for application to the chest of the patient:

an electricity source for applying current between said electrodes to pass through the chest of the patient;

a circuit which is coupled to said electrodes and which has an output that carries signals representing changes in impedance encountered by said current that represent cardiopulmonary activity of the patient;

an analyzing circuit with an input that receives said signal representing the cardiopulmonary activity of the patient, and which determines the average frequency of those signals representing heartbeat rate and those signals representing breathing rate, wherein:

said analyzing circuit is constructed to indicate no cardiac arrest when the heart rate is above about 20 beats per minute and the respiratory rate is above about 4 breaths per minute.

3. Apparatus for evaluating the condition of a patient who has symptoms of cardiopulmonary arrest comprising:

a pair of electrodes for application to the chest of the patient:

an electricity source for applying current between said electrodes to pass through the chest of the patient;

a circuit which is coupled to said electrodes and which has an output that carries signals representing changes in impedance encountered by said current that represent cardiopulmonary activity of the patient;

an analyzing circuit with an input that receives said signal representing the cardiopulmonary activity of the patient, and which determines the average frequency of those signals representing heartbeat rate and those signals representing breathing rate; wherein said analyzing circuit is constructed to indicate extreme brady arrhythmia when the respiratory rate is above about 4 breaths per minute but the heart rate is below about 20 beats per minute.

4. Apparatus for evaluating the condition of a patient who has symptoms of cardiopulmonary arrest comprising:

a pair of electrodes for application to the chest of the patient:

an electricity source for applying current between said electrodes to pass through the chest of the patient;

a circuit which is coupled to said electrodes and which has an output that carries signals representing changes in impedance encountered by said current that represent cardiopulmonary activity of the patient;

an analyzing circuit with an input that receives said signal representing the cardiopulmonary activity of the patient, and which determines the average frequency of those signals representing heartbeat rate and those signals representing breathing rate; wherein said electricity source is constructed to generate current whose amplitude varies at a frequency that is at least 1000 Hz and less than 90 kHz, whereby to provide a current whose frequency is far above the cardiopulmonary frequency of interest and that has minimal inductive and capacitive reactance.

5. Apparatus for evaluating the condition of a patient who has symptoms of cardiopulmonary arrest comprising:

a pair of electrodes for application to the chest of the patient;

an electricity source for applying current between said electrodes to pass through the chest of the patient;

a circuit which is coupled to said electrodes and which has an output that carries signals representing changes in impedance encountered by said current that represent cardiopulmonary activity of the patient;

an analyzing circuit with an input that receives said signal representing the cardiopulmonary activity of the patient, and which determines the average frequency of those signals representing heartbeat rate and those signals representing breathing rate; and a defibrillator generator circuit which is coupled to said electrodes to apply a defibrillating pulse to the patient through said electrodes.

6. Apparatus for evaluating the condition of a weak patient, comprising:

a pair of electrodes for application to the chest of the patient;

an electricity source for applying a voltage between said electrodes to flow current between them;

a circuit which is coupled to said electrodes and which detects impedance encountered by said current and which has an output that carries signals representing the cardiac activity of the patient, said circuit including a filter that passes only signals of a frequency greater than at least about 0.3 Hz to filter out impedance changes caused by respiration of the patient;

means that indicates blood pressure of the patient based on said impedance.

7. The apparatus described in claim 6 wherein:

said means that indicates blood pressure, indicates both systolic pressure and diastolic pressure.

8. Apparatus for evaluating the condition of a patient who has symptoms of cardiopulmonary arrest comprising:

a pair of electrodes for application to the chest of the patient;

an electricity, source for applying current between said electrodes to pass through the chest of the patient;

a circuit which is coupled to said electrodes and which has an output that carries signals representing changes in impedance encountered by said current that represent cardiopulmonary activity of the patient;

an analyzing circuit with an input that receives said signal representing the cardiopulmonary activity of the patient, and which determines the average frequency of those signals representing heartbeat rate and those signals representing breathing rate;

said circuit is constructed to deliver signals representing the volume of breath of the patient, as a function of said impedance.

9. A method for evaluating the condition of a weak patient who has symptoms indicating cardiac arrest, comprising:

applying a pair of electrodes to the chest of the patient;

applying a voltage between said electrodes to pass a current between them and through the chest of the patient;

detecting variations in said current which represent changes in impedance caused by any cardiac activity of the weak patient; wherein said step of detecting variations in said current, includes not detecting variations of a frequency at which the patient would be expected to breathe, said frequency at which the patient would be expected to breath being below one Hertz.

10. A method for evaluating the condition of a weak patient who has symptoms indicating cardiac arrest, comprising:

applying a pair of electrodes to the chest of the patient;

applying a voltage between said electrodes to pass a current between them and through the chest of the patient;

detecting variations in said current which represent changes in impedance caused by any cardiac activity of the weak patient; and detecting variations in said current which represent changes in impedance caused by any breathing of the patient, including detecting variations of a frequency below about two Hertz.

11. A method for evaluating the condition of a weak patient who has symptoms indicating cardiac arrest, comprising:

applying a pair of electrodes to the chest of the patient;

applying a voltage between said electrodes to pass a current between them and through the chest of the patient;

detecting variations in said current which represent changes in impedance caused by any cardiac activity of the weak patient; wherein said step of applying a voltage includes applying a voltage that varies sinusoidally in amplitude and that has a frequency between 1000 Hz and 90 kHz.

12. A method for evaluating the condition of a weak patient who has symptoms indicating cardiac arrest, comprising:

applying a pair of electrodes to the chest of the patient;

applying a voltage between said electrodes to pass a current between them and through the chest of the patient;

detecting variations in said current which represent changes in impedance caused by any cardiac activity of the weak patient;

indicating cardiac arrest of the patient when variations in said current indicate beating of the heart at a frequency less than about 20 beats per minute.

13. A method for evaluating the condition of a patient who has symptoms of cardiac arrest, comprising:

applying a pair of electrodes to the chest of the patient;

applying a voltage between said electrodes to pass a current between them and through the chest of the patient, whose said current is too low to cause a noticeable reaction in any patient;

detecting variations in said current which represent changes in impedance caused by any cardiac activity of the patient, and also detecting changes in impedance caused by any breathing activity of the patient; wherein said step of detecting changes in impedance caused by any cardiac activity includes detecting variations in impedance at a frequency which is at a rate of at least 0.3 Hertz; and said step of detecting changes in impedance caused by any breathing activity includes detecting variations in impedance of a frequency which is below about 0.3 Hertz.

* * * * *